United States Patent
Fay, Jr.

(10) Patent No.: US 7,238,954 B1
(45) Date of Patent: Jul. 3, 2007

(54) OPTICAL EXTERNAL CAVITIES HAVING BREWSTER ANGLE WEDGES

(76) Inventor: Theodore Denis Fay, Jr., 21911 Bacalar Dr., Mission Viejo, CA (US) 92691

(*) Notice: Subject to any disclaimer, the term of this patent is extended or adjusted under 35 U.S.C. 154(b) by 124 days.

(21) Appl. No.: 10/959,490

(22) Filed: Oct. 6, 2004

Related U.S. Application Data

(60) Provisional application No. 60/509,460, filed on Oct. 8, 2003.

(51) Int. Cl.
*G01J 1/58* (2006.01)
*G01N 21/64* (2006.01)

(52) U.S. Cl. .................................. 250/458.1
(58) Field of Classification Search ............. 250/458.1
See application file for complete search history.

(56) References Cited

U.S. PATENT DOCUMENTS

| | | | |
|---|---|---|---|
| 4,577,110 A * | 3/1986 | MacBride et al. | 250/461.2 |
| 4,661,711 A * | 4/1987 | Harjunmaa | 250/458.1 |
| 5,491,344 A | 2/1996 | Kenny | |
| 5,617,206 A | 4/1997 | Fay | |
| 6,118,127 A | 9/2000 | Liu | |
| 6,121,053 A | 9/2000 | Kolber | |
| 6,236,456 B1 | 5/2001 | Giebeler et al. | |
| 6,255,118 B1 | 7/2001 | Alfano et al. | |
| 6,369,894 B1 | 4/2002 | Rasimas et al. | |
| 2002/0149769 A1 * | 10/2002 | Roorda et al. | 356/318 |
| 2002/0186743 A1 * | 12/2002 | Tani et al. | 372/92 |
| 2003/0178577 A1 * | 9/2003 | Aronkyto | 250/458.1 |

* cited by examiner

*Primary Examiner*—David Porta
*Assistant Examiner*—Mark R. Gaworecki
(74) *Attorney, Agent, or Firm*—Walter A. Hackler

(57) ABSTRACT

A fluorometer having extremely high spectral resolution and the capability of blocking exciting light. The fluorometer is inexpensive and rugged since it may comprise a device with no moving parts. The fluorometer comprises the following main components, a light input for receiving the fluorescing light, a collimating lens, a Fabry-Perot etalon, two dichroic mirrors, a Brewster angle wedge prism, and an output for reading the fluorescence.

15 Claims, 4 Drawing Sheets

The Compact Echelle Fluorometer with the Brewster Angle Wedge

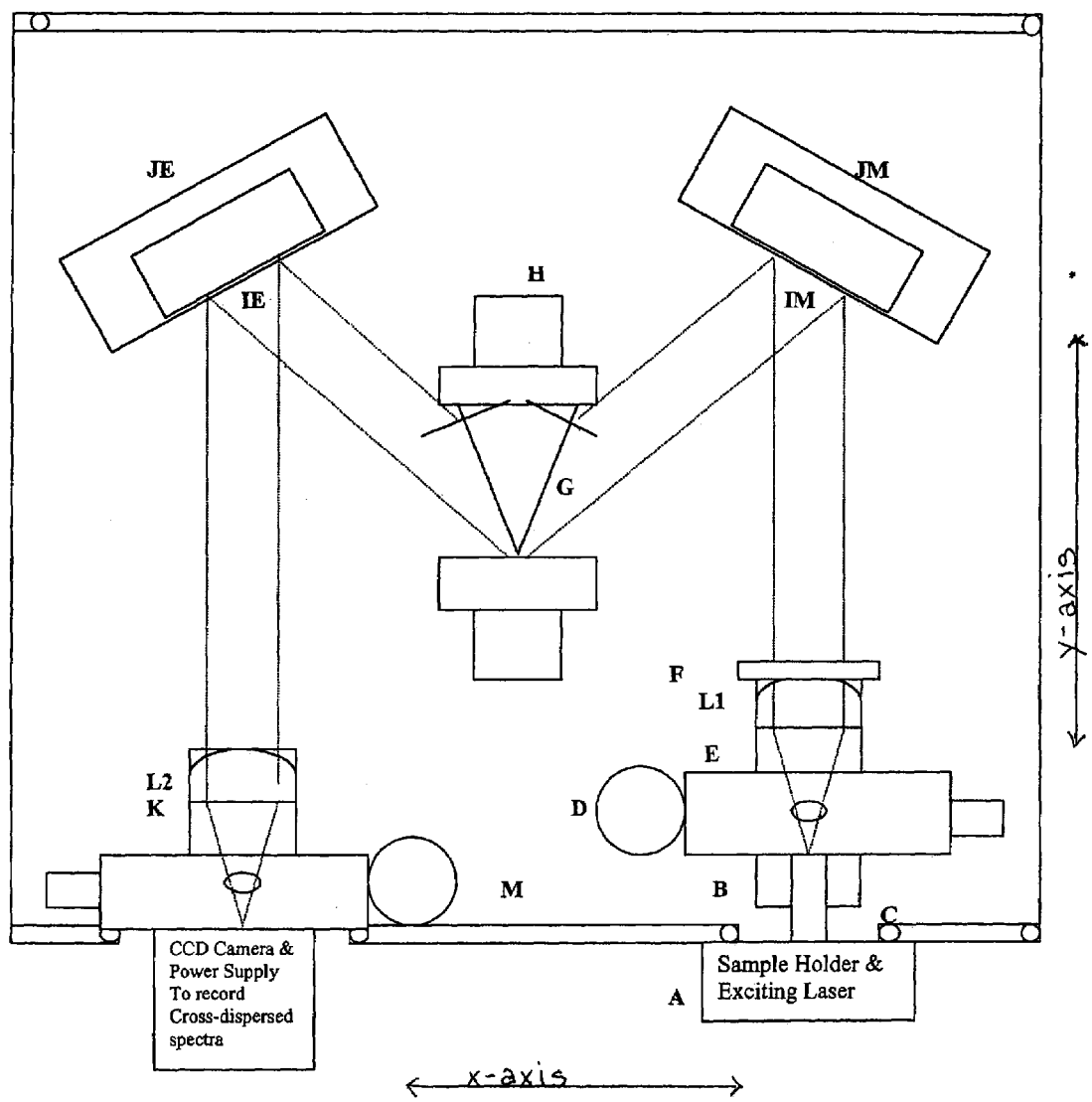
Figure 1. The Compact Echelle Fluorometer with the Brewster Angle Wedge

Figure 2/2. Component Vendor Parts for the Compact Fluorometer
N. Thor Labs, Newton, NJ, SM1-PT, Q. Thor Labs Fibers AFS-105, 125Y,
, D&M. Thor Labs Newton, NJ, ST1-XY-S, L1 and L2. Opto,
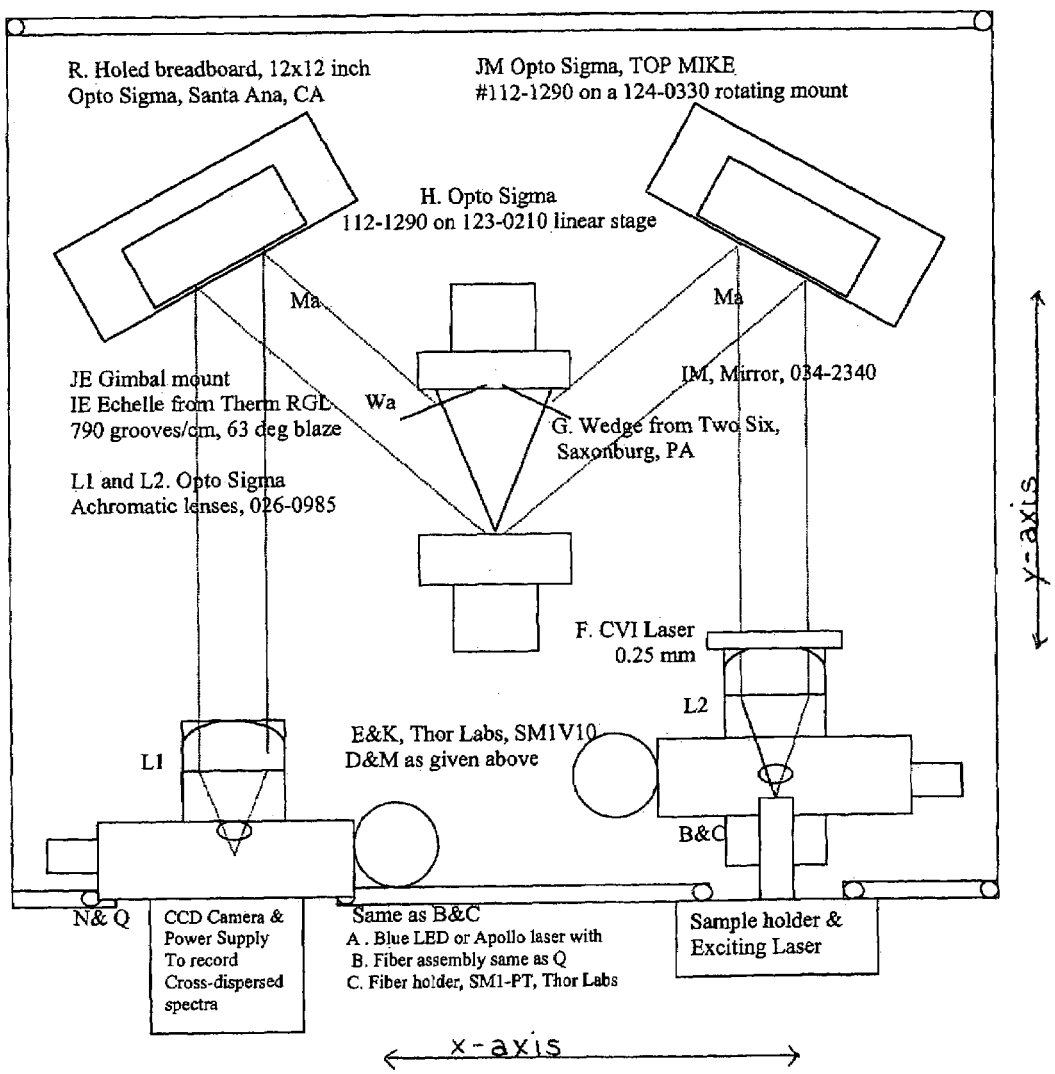

Table 1
Description of Optical Components Labeled on the Previous Figure

| Figure | Optical Component | Description of Function |
|---|---|---|
| A | Sample container | Accepts excitation light From source fiber |
| B | Fiber column | Connects sample and collimator |
| C | Mount for input fiber | Hold fiber assembly to D1 and D2 |
| D1 | Mounting tube for lens, L1 | Holds collimator lens in place |
| D2 | Translation stage, XY For input assembly | Micrometer adjustment associates a given fiber with a given Fabry-Perot fringe pattern |
| L1 | Collimator lens for Fabry Perot and wedge | Collimate light from input Fibers |
| F | FP or Fabry-Perot etalon filter First active wavelength Adjustment element | Isolate fluorescent wavelengths spatially and spectrally at 30 times the resolution of the prism |
| G | Two Six ZnS wedges Have twice the dispersion of low order gratings | Disperses light at 1 pixel/10cm-1 Separates Fabry-Perot fringes and echelle orders. |
| H | Three axis rotation holder for Two Six wedge | Adjusts dispersion and incident angle of spectrum onto echelle By cross dispersion |
| JM | TOP MIKE mount for mirror rotates mirror | the flat mirror directs the light from the collimation lens to the wedge |

| Figure | Optical Component | Description of Function |
|---|---|---|
| IM | Mirror | Transmits dispersed spectra To the ZnSe wedge |
| JE | Adjustable mount For the echelle grating | The JE mount gimbals the echelle vertically to the 63-degree blaze angle |
| IE | Echelle grating Disperses the light Into many orders | Echelle disperses at 1.2 pixel/cm-1 at a wavelength of 600 nm, second embodiment has a flat mirror like IM |
| K | Camera lens tube | Focus and hold output lens |
| L2 | Camera lens | Output version of Lens L1 |
| M | Translation stage for Output assembly | Micrometer position gives a fine adjustment of specific Wavelengths |
| N | Breadboard, 8 x 8 inches All mounts are held by Thor Labs RB2 and RS2 posts Together with dual RM1C clamps | Bolt attachment holes for components on every square inch on board Post positions are shown by dual circles on Figures 1 and 2 |

OPTICAL EXTERNAL CAVITIES HAVING BREWSTER ANGLE WEDGES

PRIORITY DATA

This application claims priority to U.S. Provisional Application 60/509,460 filed on 8 Oct. 2003.

FIELD OF THE INVENTIONS

The inventions described below relate the field of fluorometers, in particular to those using dispersive optics.

BACKGROUND OF THE INVENTIONS

The basic optics of dispersive and filter devices used to record the fluorescent spectra have remained relatively constant during the past several decades. A brief survey of the inventions in this field shows that there are few fundamental innovations in filters, prisms, wedges and gratings components used in this field of spectroscopy. In contrast there are hundreds of novel patents that concern innovative fluorescent tags and light sources to implement ever more specialized biological and chemical applications.

There has been some work in the field of fluorometers. Alfano (2001) disclosed an all-solid state fluorometer that uses either blue LEDs or red laser diodes as the exciting fluorescent sources. Lui and Li (1999) disclose a transmission grating fluorometer for DNA sample identification. Their method uses four dyes, one tag for each nucleotide. Kenny and Taylor (1996) disclose a fluorometer using a $3^{rd}$ or $4^{th}$ harmonic Nd:YAG laser. The emitting laser wavenumbers are 28200 and 37594 cm−1. They used a mixture of H2 and CH4 gas to Raman shift the laser light to the appropriate fluorescent dye excitation wavelengths. The spectral wavenumber options for excitation occur at integer multiples of these Raman shifts (about 3000 and 3600 cm−1); all wavenumbers lie below the Nd:YAG harmonic wavenumbers, such as 28200. cm−1.

Others have also used continuum spectral sources such as high-pressure Xenon gas sources and solid-state tungsten filaments to excite fluorescent dyes. This approach normally requires a monochronometer or other added filter to isolate the exciting wavelengths. Rasimas, Fehr and Hoots (2002) use a grating monochronometer to restrict the excitation wavelengths. Their device has the advantage of a being a tunable source, accomplished by turning the grating, if the spectral output is confined with a narrow exit slot. Giebler, Ogle and Kay (2001) use a similar exciting source; they also use a second grating monochronometer to measure the fluorescent light that arises from exposing the target sample to the exciting light. Other inventors, such as Kolber and Falkowski (2000) use a pulsing source to measure the time response of the fluorescent light. They do this using flashlets or brief flashes of light from a continuum Xenon source. This technique helps isolate the fluorescent source from the scattered light from the exciting source.

There is a need for a novel fluorometer that absorbs the light from the exciting source while transmitting the fluorescent light to the detector. This fluorometer must have higher dispersion than conventional optics so that the fluorometer can become as compact as the current microcomputers and have a high spectral resolution.

The following is a list of references, each of which is incorporated herein by reference:

Alfano, et al 2001 "Method for Using an All Solid State Fluorometer in an Industrial Water System Application", U.S. Pat. No. 6,255,118, 3 Jul. 2001, Assignee: NALCO Chemical Company, Naperville, Ill.

(2) Kenny, J. and Taylor, T. 1996 "Method and System for Examining the Composition of a Fluid or Solid Sample Using Fluorescence and or Absorption Spectroscopy", U.S. Pat. No. 5,491,344, 13 Feb. 1996, Assignee: Tufts Univ., Medford, Mass.

(3) Liu, C. and Li, Q. 2000 "Detector Having a Transmission Grating Beam Splitter for a Multi-Wavelength Sample Analysis", U.S. Pat. No. 6,118,127, 12 Sep. 2000, Assignee: Spectrumedix Corp., State College, Pa.

(4) Rasimas, J. Fehr, M. and Hoots, J. 2002 "Modular Fluorometer", U.S. Pat. No. 6,369,894, 9 Apr. 2002, Assignee: NALCO Chemical Company, Naperville, Ill.

(5) Giebler, R. and Ogle, D. and Kaye, R. 2001 "Optical System for a Scanning Fluorometer", U.S. Pat. No. 6,316,774, 12 Nov. 2001, Assignee: Molecular Devices Corp, Sunnyvale, Calif., See also U.S. Pat. No. 6,236,456, on 22 May 2001 by the same authors.

(6) Kolber, Z. and Falkouski, P. 2000 "Multiple Protocol Fluorometer and Method", U.S. Pat. No. 6,121,053, 19 Sep. 2000, Assignee; Brookhaven Science Associates, Upton, N.Y.

SUMMARY

The major issues with the current fluorometer technology can be overcome by using a high dispersion Brewster angle wedge as the dispersive element of the fluorometer. Wedges made of most optical materials have not been favored in most fluorometer designs in the past, because the optical materials considered have factors of 10 or more lower dispersion and resolution than gratings.

The fluorometer has a spectral resolution that can be varied from 75,000 to 750,000. It has very high dispersion components for high spectral resolution in a compact package. The present prototype is compact, less than 30×30 cm in area and only 16 cm high. The fluorometer achieves this resolution by placing a Fabry Perot etalon in tandem with an echelle grating. The echelle orders are separated by a new type of cross dispersion device, a Brewster angle wedge made from II VI materials such as ZnSe and ZnS. The spectra are recorded with a charge coupled device camera. A light emitting diode or a blue laser is the exciting light source for the fiber/polymer optrode sensor. Many of these fibers carry the fluorescence from the optrode to the analyzing optics. The II VI wedge has 10 times the dispersion of commercial glass prisms, and they have 90% transmission, as well as less than 3% reflected light. It, the echelle and the Fabry Perot increase the throughput (solid acceptance angle) as well as the speed of the fluorometer by a factor of 4 over conventional designs. The fluorometer also has about 4 times the spectral resolution of the competitive Michelson designs. It has greater spectral and spatial resolution than most Michelson interferometers by a fraction of the ratio of the finesse of the Fabry Perot of the same size, typically a factor of 12 for a Fabry Perot finesse=50. Both the dichroic mirrors and the wedge block the exciting light. The blockage efficiency is 24 orders of magnitude, 12 in the wedge and 6 in each of the dichroic mirrors. It transmits the fluorescent light with 70% efficiency. There is a 10% light loss in the wedge, 20% in the echelle and about 2% in the lenses and dichroic mirrors combined at the fluorescence wavelengths between 540 and 700 nm.

BRIEF DESCRIPTION OF THE DRAWINGS

FIG. 1 shows the position of the optical components in a Brewster-angle-wedge fluorometer.

FIG. 2 shows the device of FIG. 1 and specifies the vendors that are capable of selling each component.

DETAILED DESCRIPTION OF THE INVENTIONS

FIG. 1 shows the position of the optical components in a Brewster-angle-wedge fluorometer. The diode laser or LED is the exciting source as shown on the right side of FIGS. 1 and 2, is designated as A; this source irradiates the sample creating the fluorescence signal. Very low (picomolar or less) amounts of fluorescent agent create a very low signal relative to the exciting light. The mount labeled C holds the input fiber assembly, B, which transmits the fluorescent light and some scattered exciting light to the fluorometer optics. Current fluorometers only use interference filters to block this exciting light to about 6 orders of magnitude, greatly limiting their sensitivity (a factor of a million reduction in exciting light is not enough for many important applications of fluorometers).

The translation stages D and M hold the input and output fiber assemblies C and N. They hold the corresponding collimator lenses E and K. These two translation stages control the positions of the lenses, L1 and L2, relative to their respective fiber assemblies to within one half micron. Small shifts in these translations enable the user to select the order of the Fabry Perot, F (Y axis for D and M) and the dispersion between these orders, using the ZnSe (or other II-VI) wedge, G (X axis for D and M). The optics transmits the fluorescent light and blocks the exciting light entering the fluorometer from given input fiber. A charge coupled device camera then records the fluorescent light from many fibers.

The translation stage, D, determines the positions of the input fibers relative to the ZnSe wedge (X axis) and the Fabry Perot (Y axis). For each input fiber there will be a corresponding output fiber for any given angle of the mirror IF shown in FIGS. 1 and 2. Thus any given set of wavelength bands can be selected for transmission output by properly positioning the X and Y axes of the output fiber assembly translation stage M. Different narrow spectral bands then enter each of the output fibers located at slightly different X and Y axes positions as determined by the angular dispersions of the components. In first prototypes built for sale the stages D and M are adjusted by hand held micrometers. In later prototypes these four axes will be controlled by automatic means, such as piezo-electric transducers.

For Fabry-Perot etalons with a thickness of one centimeter, spectral channels may be as narrow as 0.001 nm wide at near infrared wavelengths and may be several times smaller at visual wavelengths. The resolution of the spectral pass bands depend on the thickness of these etalons and their finesse. The etalon finesse increases with the reflectivity, smoothness and flatness of the plates. Typical etalon thickness values for these applications range between 0.025 cm and several cm. The actual width of the spectral pass band in wavenumber units is inversely proportional to the finesse of the etalons, typically about 50, times a quantity known as the free spectral range. This free spectral range is the reciprocal of twice the etalon thickness times its refractive index. The etalon material used is typically fused quartz or silica, with a refractive index of about 1.5 at visual and near infrared wavelengths.

The Brewster angle wedge serves to simultaneously disperse the incoming fluorescent light and block the exciting blue light (to about 12 orders of magnitude—the dichroic mirrors, combined, reduce the exciting light by another 12 orders of magnitude for a total blockage of exciting light by 24 orders of magnitude). Fay (1997) first demonstrated the utility of high dispersion materials to Raman spectroscopy and laser diode compact monitors. However, the high dispersion materials have not been used in a Brewster angle wedge for fluorometer devices as proposed here. In embodiments we have already constructed, Brewster angle wedges have been made from high dispersion materials like ZnS (Cleartran), ZnSe and SFL-6 glass by our vendors (Two Six and Janos Corporations) as examples for our fluorometer wedges. These three different materials were carefully selected to provide a range of dispersions and resolutions greater than a factor of five. They have transmission limits that range from 300 nm for the SFL-6 glass to 550 nm for ZnSe. The materials were chosen to operate across the wavelength range (350 to 800 nm) used by more than 90% of today's fluorescence applications.

The lens collimation optics and the required fiber optics are available from many optical companies, including Newport Optical, Edmonds Scientific, Opto Sigma and Thor Laboratories. The required initial adjustments for the fluorometer can be set using commercial micrometer mounts from companies such as Thor Laboratories and Opto Sigma Corporation. The dispersion devices cannot be tilted by Piezo-electric in most fluorometers available commercially. However, in several embodiments of the fluorometer the beam is tilted slightly by acousto optic means. Such crystals are available from Brimrose Corporation and Crystal Technology.

Different embodiments of the invention are possible in addition to those shown in the figures of this provisional patent. As mentioned above, the instrument can easily be put under motorized translation stages available either from New Focus or Opto Sigma. These are activated in each case by their patented piezoelectric means, which are under computer control. They will make possible an automatically tunable fluorometer whose fabrication costs are very low because they can be fabricated from the components listed in FIG. 2 in a few hours per unit.

Semiconductor wedge embodiment: The coated mirror, labeled IM, has a two axis kinematic mount labeled JM. The user adjusts this mirror so as to direct the laser light toward the wedge at an angle such that laser light passes repeatedly through the wedge parallel to the base as shown in FIGS. 1 and 2. The circular wedge, G is held at the proper dispersion angle by a rotation tube positioned inside the dual axis mount, H. The coated mirror, labeled IM, has a two axis kinematic mount labeled JF. Only those narrow laser wavelength bands and polarization modes dispersed by the wedge toward the normal of the mirror IM are reflected back toward the camera or avalanche diode for measurement. The exciting light and scattered room light are not recorded (blocked by the band gap of the wedge and by the coatings on the mirrors). The orientation of the IM mirror enables light to enter the wedge near the Brewster angle. The output, or IE mirror and its mount JE, transmit a small fraction of this given wavelength toward a particular location toward a camera assembly.

Fabry Perot embodiment: As previously described, the X and Y micrometers of the mount D change the positions of the input fiber assemblies relative to the dispersive components of the fluorometer. FIG. 1 designates these components as follows: Fabry Perot etalon filter, F, and the wedge, G. The Y-axis of the D stage determine the wavelengths transmitted by the fringes of the Fabry Perot. The wedge displaces these multiple fringes along the X-axis by an amount determined by the input angle. In this way, the X and Y micrometers of the D stage will alter the positions at the output fiber assembly (M) relative to the wavelengths reflected from the input by the mirror IM. Fine adjustments in the X and Y positions change both the wedge and Fabry Perot fringe pattern location.

In all embodiments, the input and output micrometer motions on the translation stages have locks on both the X and Y-axes. The mounts that hold the fiber assemblies to the translation stages, C and N, have external class 40 threads that are about 1.008 inches external diameter. The translation stage has the same size internal thread, which has an ID of 1.008 inches and is also a class 40 thread. Both the C and N mounts can accommodate an assembly of fibers with a diameter of 6.4 mm or about 6400 microns. Since each fiber has a diameter of 10 microns, the maximum number of fibers possible is not more than $(6,400/10)^2$ or a little over 400,000 fibers. In near term applications the fiber cladding diameter will limit the number of fibers used to not more than a few thousand.

The high throughput of the wedge optics shown in FIGS. 1 and 2 can accommodate hundreds of fibers, because of the high index of refraction of the wedge and the large field of view of the Fabry Perot optics. The following sentences quantify the capacity and accuracy of the output fibers to transmit pure spectral bands. Each fiber can have a diameter (of the transmitting core) as small as 10 microns. The smallest graduations on the four D and L micrometer scales are about 0.5 micron. Thus the translation stage adjustments enable the user to standardize a repeatable calibration fringe pattern within 1/20 of the diameter of a given fiber. Each different fiber can be made to transmit a specific wavelength of light to the end stage application, typically a fluorescence spectrometer or telecommunications device. The larger the individual fiber diameters; the better the user can center the spectral images. If the micrometers are moved by several of these graduations, the calibration may change slightly.

Fluorometers must be adjusted so that the light from many fibers can be accurately measured by the detector. These adjustments require that the fluorometer mirror reflect light from different fibers in both wedge and wedge plus echelle grating embodiment onto different picture elements of the recording camera. This requires high dispersion of both the wedge and the echelle, so that different fiber input angles and wavenumber band passes are discriminated. Many fluorometers require both long focal lengths and one or more fibers to accomplish this goal. These fibers can only detect one agent at a time. The grating equations are related to the differential of the grating equation for the diffraction angle, $\Delta\theta d$ times the distance between the centers of the grating and pivot mirror, hm. Current gratings give an equation for the change in the optical path, $\Delta P$ in cm, of the pivot translation length versus unit wavenumber, $\Delta\omega$ in cm−1, is given by (1):

$$\Delta P/\Delta\omega = hm\Delta\theta d = hmSM/\omega\omega, \quad (1)$$

where hm is in cm, $\omega$ is the wavenumber in cm−1, S is the grating parameter or the number of grooves per cm, and M is the grating order number, usually a small integer.

The grating equation for the change in the independent pivot rotation angle, $\theta p$, per unit wavenumber, $\Delta\omega$, is given by (2):

$$\Delta\theta p/\Delta\omega = [4\omega^3 + 2\omega\Delta\omega SM(1-\sec\theta r\tan\theta b)]/\omega^4 \sec\theta p$$
$$\tan\theta p =$$

or approximately $4/\omega \sec\theta p \tan\theta p$, (2)

where $\theta r$ is the reflection angle of the grating relative to the input laser beam and the normal to the grating and $\theta b$ is the grating blaze angle.

These equations show that the motions required for the pivot mirror in prior art devices are complex and highly non linear, greatly complicating the scanner and data reduction from the detector. Note that equation (1) depends on both the grating parameter and the reciprocal square of the wavenumber and that (2) the equation is quite non linear in the pivot angle and also depends on the reciprocal of the wavenumber. The user must simultaneously align two angles in the pivot motion equation and contend with different relations for wavenumber dependence. These facts rule out a simple translation of the input beam control mirror. Hence, design and fabrication of dual mirror pivot mounts are expensive and are a major reason why precision external cavities cost $25K, even in mass production. It follows that precision fluorometers and Raman spectrometers and other sensors that utilize such cavities to stabilize the light source will cost twice as much as the spectrometer or fluorometer alone.

On the other hand, the wedge fluorometer described herein uses a Brewster angle wedge to simplify fluorometer design, reduce costs and increase alignment accuracy. The two controlling equations for the Brewster angle wedge are based on the change in the wedge dispersion versus wavenumber. These equations can be simplified in the Brewster angle case to the simple relations (3) and (4) below:

$$\Delta P/\Delta\omega = 2(\Delta nw/\Delta\omega)D, \quad (3)$$

$$\Delta\theta w/\Delta\omega = 2(\Delta nw/\Delta\omega), \quad (4)$$

where D is the constant diameter of the circular wedge and $(\Delta nw/\Delta\omega)$ is the change of the bulk index of refraction of the wedge with wavenumber. Both translation and angle have the same dependence on wavenumber. The refractive index varies directly with the wavenumber, modified by the Sellmeier constants of the wedge material. The path and the angle of the input beam are directly related to wavenumber only by this refractive index gradient. This means that if the focal length of this input beam is approximately equal to D, then a simple translation of the beam will meet the requirements of equations 3 and 4, as the laser wavenumber is varied. Hence a simple translation of the beam is easy to achieve with either a fiber input lens and micrometer means or by changing the voltage on an acousto optical crystal inserted in the beam. Either method will be less expensive, more accurate and less costly than the complex reflector pivot motions required by equations (1) and (2) for the grating.

Other Advantages of the Brewster Angle Wedge Over the Low Order Grating

There are additional advantages to using a Brewster angle wedge in the fluorometer as opposed to a grating. These advantages include increased photon efficiency of the fluorometer, higher dispersion (wavenumber sensitivity) and higher spectral resolution. The equations and tables below are a comparison between the performance of the Brewster angle wedge and gratings used in low order. An exception to this rule is when the Brewster angle wedge is used with a high dispersion echelle grating. This is claimed here as an innovation The Brewster angle wedge spectral resolution computed in Table II is given by (5a):

$$(\omega/\Delta\omega)p = Bl\omega(\omega dnw/d\omega) \quad (5a)$$

where Bl is the projected wedge base length. This is twice the wedge circular diameter, D times the tangent of the wedge half angle α. The diffraction of the light within the wedge limits the resolution, and this formula results from the usual Rayleigh resolution criterion. Typical values for ZnSe wedges around 590 nm are: dnw/dω=0.3 per micron−1 and o=1.7 micron−1, so that ωdnw/dω=0.5. The numbers given in Table II are apply to the sample II VI wedges with Bl=2 cm, about the size of the prototype hardware described by the Figures.

Diffraction also limits the grating resolution as given by (5b):

$$(\omega/\Delta\omega)g = Bg\omega(\sin ig + \sin id) \quad (5b)$$

Where Bg is the width of the ruled surface (assume Bg=Bl to compare performance) and ig is the input laser beam angle relative to the grating normal. The angle id is the diffraction angle measured from the grating normal. The numbers given in Table II assume that the sum of the sines of the angles in (5b) is kept below 0.4 to increase grating efficiency and reduce scattered laser light as described in the previous section.

The analogous formula for the spectral resolution of the Fabry Perot etalon is given by (5c):

$$(\omega/\Delta\omega)e = Be\omega 2ne\, Fe \quad (5c)$$

Where ne is the etalon refractive index (about 1.5) and Fe is its finesse. In the ideal case of extreme flatness of the etalons, $Fe=(pi\sqrt{r})/(1-r)$ or about 50, if r=0.94, as is typical for modern ZnS coatings of quartz plates at 600 nm. CVI Laser can now mass produce etalons of this quality at low cost. This is why the etalon resolution can be more than 150 times greater than either grating or prism for an etalon thickness, Be, approximately equal to Bg or Bl.

The wedge linear dispersion versus wavenumber computed in Table III is given by (6a):

$$(\Delta x/\Delta\omega)p = 2Fc(\omega BmCm^2/np(1-Cm^2\omega^2)^2.$$
$$(\sin \alpha \sec \theta) \quad (6a)$$

where, Fc is the focal length of the camera fiber optics, np is the wedge bulk refractive index, Bm and Cm are the Sellmeier constants for the wedge material and θ is the entrance and exit angle relative to the normal to the wedge face.

The grating linear dispersion is proportional to the tangent of the blaze angle, θb:

$$(\Delta x/\Delta\omega)g = 2Fc \tan \theta b/\omega, \text{ which is also shown in Table III.} \quad (6b)$$

TABLE II

Grating Versus Wedge (Brewster Angle) Spectral Resolution

| Wavelength, nm | Wavenumber, cm-1 | Material Name | Wedge Res. $(\omega/\Delta\omega)w$ | Wedge/Grating $(\omega/\Delta\omega)w/(\omega/\Delta\omega)g$ |
|---|---|---|---|---|
| 400 | 25,000 | ZnS | 42,000 | 2.1 |
| 500 | 20,000 | ZnSe | 36,000 | 2.3 |
| 600 | 16,667 | ZnSe | 16,600 | 1.2 |

TABLE III

Grating Versus Wedge (Brewster Angle) Spectral Dispersion

| Wavelength, nm | Wavenumber, cm-1 | Material Name | Wedge Disp. $(\Delta x/\Delta\omega)p$ | Wedge/Grating $(\Delta x/\Delta\omega)p/(\Delta x/\Delta\omega)g$ |
|---|---|---|---|---|
| 400 | 25,000 | ZnS | 3.80 | 3.85 |
| 500 | 20,000 | ZnS | 1.80 | 1.70 |
| 600 | 16,667 | ZnSe | 1.90 | 1.90 |

Wedge dispersions are in microns/cm-1 for a camera focal length, Fc = 5 cm. Wedge/grating dispersions are a ratio.

Echelle embodiment: The echelle is a coarse grating (typically 800 lines or fewer per cm) operated in a high order, typically 30 or more, and requires an order sorter prism. Prototype demonstrations have shown that our Brewster angle wedge functions as an excellent order sorter prism. The wedge has such high dispersion that many input fibers can be used and their spectra can be separated on the recording camera. The resolution of the echelle is the number of the order (typically 30 or more times the total number of grating grooves, typically 4000 or more. The product of these two numbers is 120,000 or higher. The dispersion of the echelle is inversely related to the wavenumber and directly related to the tangent of the blaze angle, typically 63 degrees or more as given by equation (7):

$$Gdisp = 2Fcwbana \tan \theta b/\omega,$$

Where Fc is the cameral focal length, typically 40 mm. The grating immersion factors are na (the refractive index of air) and $$wba = (na^2 - \sin^2 \theta b)^{1/2}/\cos \theta b \quad (7b)$$

The wavenumber dispersion between orders dog is:

$$d\omega g = Sg \sec \theta di/(na\, wbs \sin \theta b \cos y) \quad (7c)$$

where θδi is the off blaze angle and gamma is the tilt angle relative to the wedge.

The echelle embodiment grating efficiency shown in Table IV is given by (8):

$$Geff = rg(1 - \sin \theta b \tan \theta r), \quad (8)$$

where rg is the reflectivity of the coating on the grating grooved face, assumed to be a dielectric coating with an efficiency of 99.%, and the other parameters are defined as in equation (2).

Equation (7) shows that echelle grating efficiency is not a function of wavelength, but is limited by both its reflectivity and blaze angles, but higher blaze angles, θb, are needed for higher grating dispersion, as given by (7). The highly desired low input reflectivity angles, θr, then result in larger fluorometer sizes, as shown in Table IV. The efficiency of the Brewster angle wedge is very high, Peff>90%, is not very sensitive to wavelength and can be further improved with dielectric coatings.

TABLE IV

Grating Efficiency Results from Equation (7)

| Reflectivity Angle In blaze angle | Mirror-Grating Distance, hm in cm | Geff, Grating Efficiency Fraction |
|---|---|---|
| 1 | 3.17 | 0.905 |
| 2 | 1.43 | 0.789 |
| 3 | 0.78 | 0.608 |

The table assumes a grating blaze angle unit is 17.5 degrees and an ideal reflectivity of 99.%.

In contrast, the wedge reflectivity, Peff, will approximately equal total efficiency (wedge absorption is small) and will exceed 90. %, at all wavelengths, between 400 and 700 nm, depending on the coatings.

The scattered light levels result from light reflected at angles off axis to the main laser beam, the designations are Slg, if due to the grating and Slw, if due to the wedge as given by Equation (9):

$$Slg=1-Geff; Slw=1-Peff. \quad (9)$$

Note that the Brewster angle wedge scattered light are thus computed to be at least 10 times lower than those for grating and mirror units of similar size, provided the anti-reflection coatings on the wedge are of the quality specified by Table IV.

Mounting Strategy

The proposed mounting strategy shown in FIGS. 1 and 2 uses two mirrors. The design enables rapid assembly and alignment, since only the wedge must be translated to change the entrance angles with changing wavelength. Both entrance and exit angles that the laser beam makes with the wedge normal, Wa, are the same and constant at each laser wavelength. They both decrease at the same rate with increasing laser wavelength as shown in the Table V below. The ZnSe wedge is said to be at minimum deviation for the light beam at the given angles. The mirror mounts JM and JE are both adjusted on a rotating stage to the precise angle, Ma, given in Table V. These Ma angles will increase at the proper rate with wavelength increase as the wedge is translated toward the top of FIGS. 1 and 2. The entrance and exit angles with respect to the wedge are labeled on these Figures and given numerically in Table V.

The wedge itself is mounted on a linear stage below the H TOP MIKE. It is mounted parallel to the holes in the breadboard on a linear stage that moves parallel to the laser light entering the fluorometer from the fibers on the right side of FIG. 1. The linear stage is adjusted for each laser wavelength as shown in the last column of Table V. All mounts are in stock items available from Opto Sigma. The mirror mount JM is oriented precisely normal to the incoming and outgoing laser beam. The coating on this mirror determines discrimination between exciting and fluorescent light in the fluorometer. Absorption losses in the coated optics are less than 1%. Measured reflectivity losses in the wedge are less than 4% in each angle of polarization.

TABLE V

Mounting Angles for Current Prototype for a 38 Degree ZnSe Wedge

| Wavelength, Nanometers | Wedge Angle, Wa Degrees | Mirror Angle, Ma Degrees | Wedge Motion microns/nanometer |
|---|---|---|---|
| 500 | 68.3 | 40.7 | |
| 550 | 62.0 | 47.0 | 34.7 |
| 600 | 58.4 | 50.6 | 16.9 |
| 700 | 54.5 | 54.5 | 8.2 |

Tests at three independent laboratories (in California, New Mexico and Indiana) have shown that high dispersion materials do have the three required characteristics for an efficient fluorometer capable of discriminating between scattered source and fluorescent light: high spectral dispersion, high resolution and low levels of scattered light. The wedges comprise semiconductor and glass materials that are normally used in the mid to long wavelength infrared regions of the spectrum. The wedges may be coated to minimize both reflection and absorption light losses at visible and near infrared wavelengths. When operated at a wedge angle that is within a few degrees of Brewster's angle, the losses will be as low as 1%, which make them nearly ideal.

If multiple modes of the Fabry-Perot are sufficiently dispersed by the Brewster angle wedge, this component may be used without the piezoelectric feedback to isolate wavelength bands that are more than 100,000 times smaller than the wavelength itself. Prototypes of such an embodiment have been fabricated and tested. (The solid Fabry Perot cavities are now available from CVI Laser Corporation.)

The fluorometer has the following capabilities: (1) the use of the wedge and the dichroic mirrors to achieve 80% transmission of the fluorescent light, (2) factors of from 2 to 4 higher dispersions than gratings, (3) a factor of 2 to 16 increase in light throughput, or angular field of view of the input optical fiber assembly, consisting of from 2 to 10,000 fibers, available from Thor Laboratories, (4) factors of from 20% to 3 times higher spectral resolution, (5) a factor of 20% higher efficiency and (6) correspondingly lower levels of scattered light by factors of 10 or more. Blockage of the excited laser light by about 24 orders of magnitude. The latter advantage greatly helps in improving the performance of the laser or LED embodiments of the exciting source. (7) Off the shelf parts reduce fabrication costs and time to levels less than that of the optical components.

The compact fluorometer described herein having high and variable spectral resolution enables a wide variety of possible application in the detection of drug agents, explosives and toxic chemicals. Users can combine the fluorometer with a wide variety of dyes and fluorescent polymer agents to achieve chemical and biological agent detection with a sensitivity of 0.1 picomolar or less and a specificity of 24 orders of magnitude. The optics discriminates between the fluorescent and exciting light with a precision that exceeds current technology by at least 12 orders of magnitude.

Other applications of the fluorometer are numerous: they include chemistry, biology, environmental science, medical laboratory tests, agribusiness laboratories and sensors for defense. The latter applications include compact, reliable and low cost detectors for explosives, chemical and biological agents. Future applications for fluorescence technology will require increasing spectral resolution and wavelength accuracy in order to make more sensitive and more specific measurements using the ever growing variety of fluorescent tags. These tags include a wide variety of man made imprinting polymers and synthesized biological agents for more precise analysis of proteins and nucleic acids.

In addition, the Brewster angle wedge may be used in any spectrometer, fluorometer, or optical cavity. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

Reference to the Original Compact Laser Diode Monitor:

Fay, T. 1997 "Compact Laser Diode Monitor Using Defined Laser Momentum Vectors to Cause Emission of a Coherent Photons in a Selected Direction", U.S. Pat. No. 5,617,206, Assignee: PHI Applied Physical Sciences, Mission Viejo, Calif., 1 Apr. 1997.

Preferred examples of the fluorometer include the following:

1. A fluorometer comprising:
an entrance aperture, said entrance aperture capable of receiving input light from a light source and restricting the spatial extent of the input light, whereby the input light becomes restricted input light after interacting with the entrance aperture;
collimating optics disposed to receive the restricted input light, said collimating optics capable of collimating the restricted input light, whereby the restricted input light becomes collimated light after interacting with the collimating optics;
a Brewster angle optical wedge disposed to receive the collimated light, said wedge comprising a semiconductor material, whereby the collimated light becomes imaged light after interacting with the wedge;
focusing optics disposed to receive the imaged light, whereby the imaged light becomes output light after interacting with the focusing optics; and
a detector disposed to detect the output light.

2. The fluorometer of 1 wherein the entrance aperture is attached to a single optical fiber.

3. The fluorometer of 1 wherein the entrance aperture is attached to an array of optical fibers.

4. The fluorometer of 1 wherein the collimating optics comprise a mirror.

5. The fluorometer of 1 wherein the collimating optics comprise a lens.

6. The fluorometer of 1 wherein the wedge material comprises a coated, II-VI clear crystal suitable for spatial and spectral imaging.

7. The fluorometer of 6 wherein the II-VI crystal comprises a material selected from the group consisting of ZnS, ZnSe and CdTe.

8. The fluorometer of 1 wherein the wedge material comprises a coated, III-V clear crystal suitable for spatial and spectral imaging.

9. The fluorometer of 8 wherein the III-V crystal comprises a material selected from the group consisting of GaP, GaAs and GaSb.

10. The fluorometer of 1 wherein the detector is adapted to electronically record spatial and spectral intensities of the output light.

11. A fluorometer comprising:
an entrance aperture, said entrance aperture capable of receiving input light from a light source and restricting the spatial extent of the input light, whereby the input light becomes restricted input light after interacting with the entrance aperture;
collimating optics disposed to receive the restricted input light, said collimating optics capable of collimating the restricted input light, whereby the restricted input light becomes collimated light after interacting with the collimating optics;
spectral separation optics, said spectral separation optics disposed to receive the collimated light, whereby the collimated light becomes spectrally separated light after interacting with the spectral separation optics;
a Brewster angle optical wedge disposed to receive the spectrally separated light, said wedge comprising a semiconductor material, whereby the spectrally separated light becomes imaged light after interacting with the wedge;
focusing optics disposed to receive the spectrally separated light, whereby the spectrally separated light becomes output light after interacting with the focusing optics; and
a detector disposed to detect the output light.

12. The fluorometer of 11 wherein the spectral separation optics comprises an echelle grating.

13. The fluorometer of 11 wherein the spectral separation optics comprises a dichroic mirror.

14. The fluorometer of 11 wherein the Brewster angle optical wedge has a base, wherein the spectral separation optics and the wedge are disposed relative to each other such that the spectrally separated light passes through the wedge parallel to the base.

15. A fluorometer comprising:
an entrance aperture, said entrance aperture capable of receiving input light from a light source and restricting the spatial extent of the input light, whereby the input light becomes restricted input light after interacting with the entrance aperture;
collimating optics disposed to receive the restricted input light, said collimating optics capable of collimating the restricted input light, whereby the restricted input light becomes collimated light after interacting with the collimating optics;
spectral separation optics, said spectral separation optics disposed to receive the collimated light, whereby the collimated light becomes spectrally separated light after interacting with the spectral separation optics;
a Brewster angle optical wedge disposed to receive the spectrally separated light, said wedge comprising a semiconductor material, whereby the spectrally separated light becomes imaged light after interacting with the wedge;
filtering optics disposed to receive the imaged light, whereby the imaged light becomes filtered light after interacting with the filtering optics;
focusing optics disposed to receive the filtered light, whereby the spectrally filtered light becomes output light after interacting with the focusing optics; and
a detector disposed to detect the output light.

16. The fluorometer of 15 wherein the filtering optics comprise a light filter.

17. The fluorometer of 15 wherein the filtering optics comprise an etalon.

18. The fluorometer of 15 wherein the focusing optics are further adapted to spatially distribute the filtered light.

19. The fluorometer of 15 wherein the Brewster angle optical wedge has a base, wherein the spectral separation optics and the wedge are disposed relative to each other such that the spectrally separated light passes through the wedge parallel to the base.

20. The fluorometer of 15 wherein the wedge material comprises a coated, II-VI clear crystal suitable for spatial and spectral imaging, said wedge material selected from the group consisting of ZnS, ZnSe and CdTe.

In addition, the Brewster angle wedge may be used in any spectrometer, fluorometer, or optical cavity. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A fluorometer comprising:
an entrance aperture, said entrance aperture capable of receiving input light from a light source and restricting the spatial extent of the input light, whereby the input light becomes restricted input light after interacting with the entrance aperture;
collimating optics disposed to receive the restricted input light, said collimating optics capable of collimating the restricted input light, whereby the restricted input light becomes collimated light after interacting with the collimating optics;

a Brewster angle optical wedge disposed to receive the collimated light, said wedge comprising a coated, clear crystal II-VI material suitable for optical and spectral imaging, whereby the collimated light becomes imaged light after interacting with the wedge;

focusing optics disposed to receive the imaged light, whereby the imaged light becomes output light after interacting with the focusing optics; and a detector disposed to detect the output light.

2. The fluorometer of claim 1 wherein the entrance aperture is attached to a single optical fiber.

3. The fluorometer of claim 1 wherein the entrance aperture is attached to an array of optical fibers.

4. The fluorometer of claim 1 wherein the collimating optics comprise a mirror.

5. The fluorometer of claim 1 wherein the collimating optics comprise a lens.

6. The fluorometer of claim 1 wherein the II-VI material is selected from the group consisting of ZnS, ZnSe and CdTe.

7. The fluorometer of claim 1 wherein the detector is adapted to electronically record spatial and spectral intensities of the output light.

8. A fluorometer comprising:

an entrance aperture, said entrance a perture capable of receiving input light from a light source and restricting the spatial extent of the input light, whereby the input light becomes restricted input light after interacting with the entrance aperture;

collimating optics disposed to receive the restricted input light, said collimating optics capable of collimating the restricted input light, whereby the restricted input light becomes collimated light after interacting with the collimating optics;

a Brewster angle optical wedge disposed to receive the collimated light, the wedge comprising a coated clear crystal comprising a III-V, material suitable for spatial and spectral imaging, whereby the collimated light becomes imaged light after interacting with the wedge;

focusing optics disposed to receive the imaged light, whereby the imaged light becomes output light after interacting with the focusing optics; and a detector disposed to detect the output light.

9. The fluorometer of claim 8 wherein the III-V material is selected from the group consisting of GaP, GaAs and GaSb.

10. A fluorometer comprising:

an entrance aperture, said entrance a perture capable of receiving input light from a light source and restricting the spatial extent of the input light, whereby the input light becomes restricted input light after interacting with the entrance aperture;

collimating optics disposed to receive the restricted input light, said collimating optics capable of collimating the restricted input light, whereby the restricted input light becomes collimated light after interacting with the collimating optics;

spectral separation optics comprising an echelle grating said spectral separation optics disposed to receive the collimated light, whereby the collimated light becomes spectrally separated light after interacting with the spectral separation optics;

a Brewster angle optical wedge disposed to receive the spectrally separated light, said wedge comprising a semiconductor material, whereby the spectrally separated light becomes imaged light after interacting with the wedge;

focusing optics disposed to receive the spectrally separated light, whereby the spectrally separated light becomes output light after interacting with the focusing optics; and a detector disposed to detect the output light.

11. The fluorometer of claim 10 wherein the Brewster angle optical wedge has a base, wherein the spectral separation optics and the wedge are disposed relative to each other such that the spectrally separated light passes through the wedge parallel to the base.

12. A fluorometer comprising:

an entrance aperture, said entrance a perture capable of receiving input light from a light source and restricting the spatial extent of the input light, whereby the input light becomes restricted input light after interacting with the entrance aperture;

collimating optics disposed to receive the restricted input light, said collimating optics capable of collimating the restricted input light, whereby the restricted input light becomes collimated light after interacting with the collimating optics;

spectral separation optics, said spectral separation optics disposed to receive the collimated light, whereby the collimated light becomes spectrally separated light after interacting with the spectral separation optics;

a Brewster angle optical wedge disposed to receive the spectrally separated light, said wedge comprising a semiconductor material, whereby the spectrally separated light becomes imaged light after interacting with the wedge;

filtering optics, comprising an etalon, disposed to receive the imaged light, whereby the imaged light becomes filtered light after interacting with the filtering optics;

focusing optics disposed to receive the filtered light, whereby the spectrally filtered light becomes output light after interacting with the focusing optics; and a detector disposed to detect the output light.

13. The fluorometer of claim 12 wherein the focusing optics are further adapted to spatially distribute the filtered light.

14. The fluorometer of claim 12 wherein the Brewster angle optical wedge has a base, wherein the spectral separation optics and the wedge are disposed relative to each other such that the spectrally separated light passes through the wedge parallel to the base.

15. The fluorometer of claim 12 wherein the wedge comprises a coated clear crystal comprising II-VI material, said wedge further suitable for spatial and spectral imaging, and wherein said II-VI material is selected from the group consisting of ZnS, ZnSe and CdTe.

* * * * *